United States Patent [19]
Häfele et al.

[11] Patent Number: 5,430,476
[45] Date of Patent: Jul. 4, 1995

[54] DEVICE FOR SUPPLYING LIGHT TO ENDOSCOPES

[75] Inventors: Ulrich Häfele, Sternenfels-Diefenbach; Michael Vögele, Kämpfelbach-Ersingen, both of Germany

[73] Assignee: Richard Wolf GmbH, Knittlingen, Germany

[21] Appl. No.: 76,308

[22] Filed: Jun. 11, 1993

[30] Foreign Application Priority Data

Jun. 24, 1992 [DE] Germany .................. 42 20 633.2

[51] Int. Cl.⁶ .................. H04N 7/18; H04N 9/04; A61B 1/06
[52] U.S. Cl. .................. 348/70; 348/270
[58] Field of Search .................. 348/70, 69, 68, 71, 348/72, 65, 270, 269, 268

[56] References Cited

U.S. PATENT DOCUMENTS

| | | | |
|---|---|---|---|
| 4,887,153 | 12/1989 | Uehara et al. | 348/70 |
| 4,951,133 | 8/1990 | Onoda . | |
| 4,983,019 | 1/1991 | Ikuno et al. | 348/68 |

FOREIGN PATENT DOCUMENTS 3908366 9/1991 Germany .

OTHER PUBLICATIONS

Brochure of Richard Wolf GmbH, "Elektronisches Video-Endoskop-System 45 000", dated May 5, 1988, 4 pages.

*Primary Examiner*—Tommy P. Chin
*Assistant Examiner*—Bryan S. Tung
*Attorney, Agent, or Firm*—Panitch Schwarze Jacobs & Nadel

[57] ABSTRACT

A device has a light source apparatus, which, as required, feeds white continuous light or sequential colored light by means of a filter device having several color surface regions and two filter discs which can be rotary driven, into a particular endoscope. One filter disc is provided with the color segments red, green and white and the other filter disc is provided with the color segments blue and white to achieve a simplified and structurally compact light source apparatus, both filter discs being arranged to be rotatable on a common rotary axis and adjustable relative to one another and fixable such that the white color segment of one filter disc covers the blue color segment of the other filter disc in a first operating position of the filter discs, and the white color segment of one filter disc is aligned to be axis-parallel with the white color segment of the other filter disc in a second operating position of the filter discs.

9 Claims, 5 Drawing Sheets

DEVICE FOR SUPPLYING LIGHT TO ENDOSCOPES

BACKGROUND OF THE INVENTION a) Field of the Invention

The invention relates to a device for supplying light to endoscopes having a light source apparatus, which, as required, feeds white continuous light or sequential coloured light by means of a filter device having several colour surface regions and two filter discs which can be rotary driven, into the particular endoscope.

b) Description of the Prior Art

A device of this type is described in U.S. Pat. No. 4,951,133. This device has a filter device which is irradiated with light from a light source apparatus in order to feed white continuous light or sequential coloured light into the light conductor at the proximal end of an endoscope. The filter device has a first revolving filter disc with the three colour segments red, green and blue and a second rotary-adjustable disc having a filter part which suppresses infra-red radiation, and free access for the white light of the light source apparatus. The second disc with its free access to the ray path of the light source is adjusted to introduce white continuous light into the light conductor of the endoscope, whereas the first filter disc is driven laterally out of the ray path of the light source. If sequential coloured light is to be fed into the light conductor, the second disc is set for infra-red suppression on its filter part and the first filter disc is returned back into the ray path of the light source. The first filter disc also requires a separate drive for the lateral drivability just explained, in addition to its rotary drive. This construction of the filter device is expensive in terms of material and cost and demands an increased space requirement.

The object of the invention consists in improving the device mentioned in the introduction such that on the one hand, as required, white continuous light or sequential coloured light may be made available as illuminating light for different types of endoscopes using a simplified, inexpensive and compact construction of the light source apparatus, and in that on the other hand the device can be used as an insert.

SUMMARY OF THE INVENTION

This object is achieved by a device for supplying light to endoscopes having a light source apparatus, which, as required, feeds white continuous light or sequential coloured light by means of a filter device having several colour surface regions and two filter discs which can be rotary driven, into the particular endoscope, characterised in that one filter disc is provided with two segments having primary colours and one white segment, and the other filter disc is provided with a segment having a third primary colour and a white segment, and in that both filter discs are arranged to be rotatable on a common rotary axis and adjustable relative to one another and fixable such that the white colour segment of one filter disc covers the colour segment of the other filter disc in a first operating position of the filter discs, and the white colour segment of one filter disc is aligned to be axis-parallel with the white colour segment of the other filter disc in a second operating position of the filter discs.

As a result of this solution, two drive motors for the filter device are omitted, because the two filter discs sit on a common drive shaft which is driven by only a single motor, and because lateral driving-out of filter discs is no longer required. Overall, a compact construction for the light source apparatus, and hence also for the device of the invention, is thus also achieved. Consequently, the device is particularly well suited as a constructional unit in the form of a so-called insert.

A preferred embodiment of the device of the invention consists in that one filter disc is arranged to be rigid on a drive shaft and the other filter disc is arranged to be freely rotatable on this drive shaft, and in that both filter discs are coupled to one another by means of a spring device. One filter disc may thus have two stops at a distance from one another, and the other filter disc may have a stop cooperating with the aforementioned stops for setting the two operating positions of the filter discs.

A fixing device is preferably assigned to the filter discs for setting their operating positions, wherein the fixing device advantageously comprises a locking mechanism for each filter disc provided with a locking notch in this case. Preferably, the fixing device comprises one brake for each filter device.

Furthermore, it is advantageous that the white colour segment of one filter disc spans an angular dimension of 120°, whereas the white colour segment of the other filter disc spans an angular dimension of 240°. Overall this embodiment of the filter device is operationally safe, very simply constructed and very inexpensive to produce.

In a further preferred embodiment, the blue colour segment of the other filter disc spans an angular dimension of 120°.

Advantageously, the device is provided with a control device for adjusting and operating the filter discs.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

DESCRIPTION OF THE PREFERRED EMBODIMENTS

Figure 1:
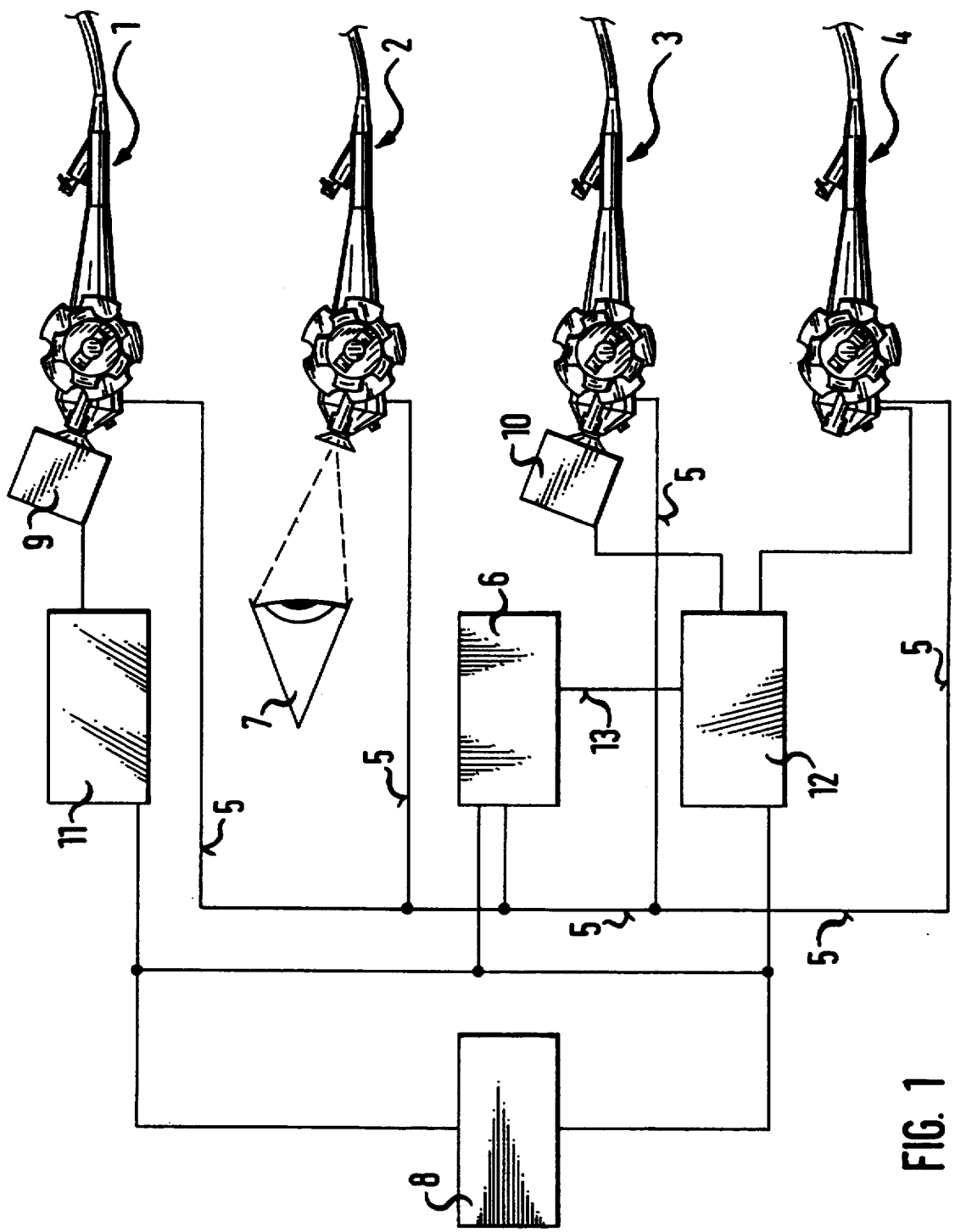
FIG. 1 shows the supply of light to different endoscopes by a single light source apparatus.

FIG. 1 shows several examples of different endoscopes 1, 2, 3 and 4, which may be connected to a single light source apparatus 6 via light conductor cable 5, in order to make illuminating light available from the apparatus 6 for the particular endoscope. The endoscopes shown are flexible endoscopes, for example fibrescopes, but they may also be rigid endoscopes. Whereas with the endoscope 2, for example a body cavity is observed with the naked eye 7 via the endoscope eyepiece, observation using other endoscopes is carried out by means of a monitor 8 and interposed solid-state image converter. The endoscopes 1 and 3 each have a solid-state image converter 9 or 10 which can be attached to its eyepiece and which is used in conjunction with a camera 11 or a videoscope processor 12 to allow the required image to appear on the monitor 8 via corresponding video signal leads, as can be seen from FIG. 1. The converter is incorporated into the distal end of the endoscope in the case of endoscope 4 (not shown).

The camera 11 with the colour CCD image converter element is assigned to the endoscope 1. White continuous light from the light source apparatus 6 is required for the endoscope 1 and also for the endoscope 2.

The black-white (B/W) CCD image converter element 10 is connected to the endoscope 3. This endoscope must therefore be supplied with sequential coloured light in order to be able to produce a colour image on the monitor 8. The endoscope 4 is a video endoscope, which is supplied both with sequential coloured light as well as with white continuous light. The sequential coloured light is required if the video endoscope is provided with a B/W CCD image converter element; and white continuous light is required if this endoscope is provided with a colour CCD image converter element. The two endoscopes 3 and 4 are also connected to the videoscope processor, which in turn is connected to the light source apparatus 6 via a control lead device 13, in order to be able to control the authorised light supply to the two endoscopes 3 and 4.

Figure 2:
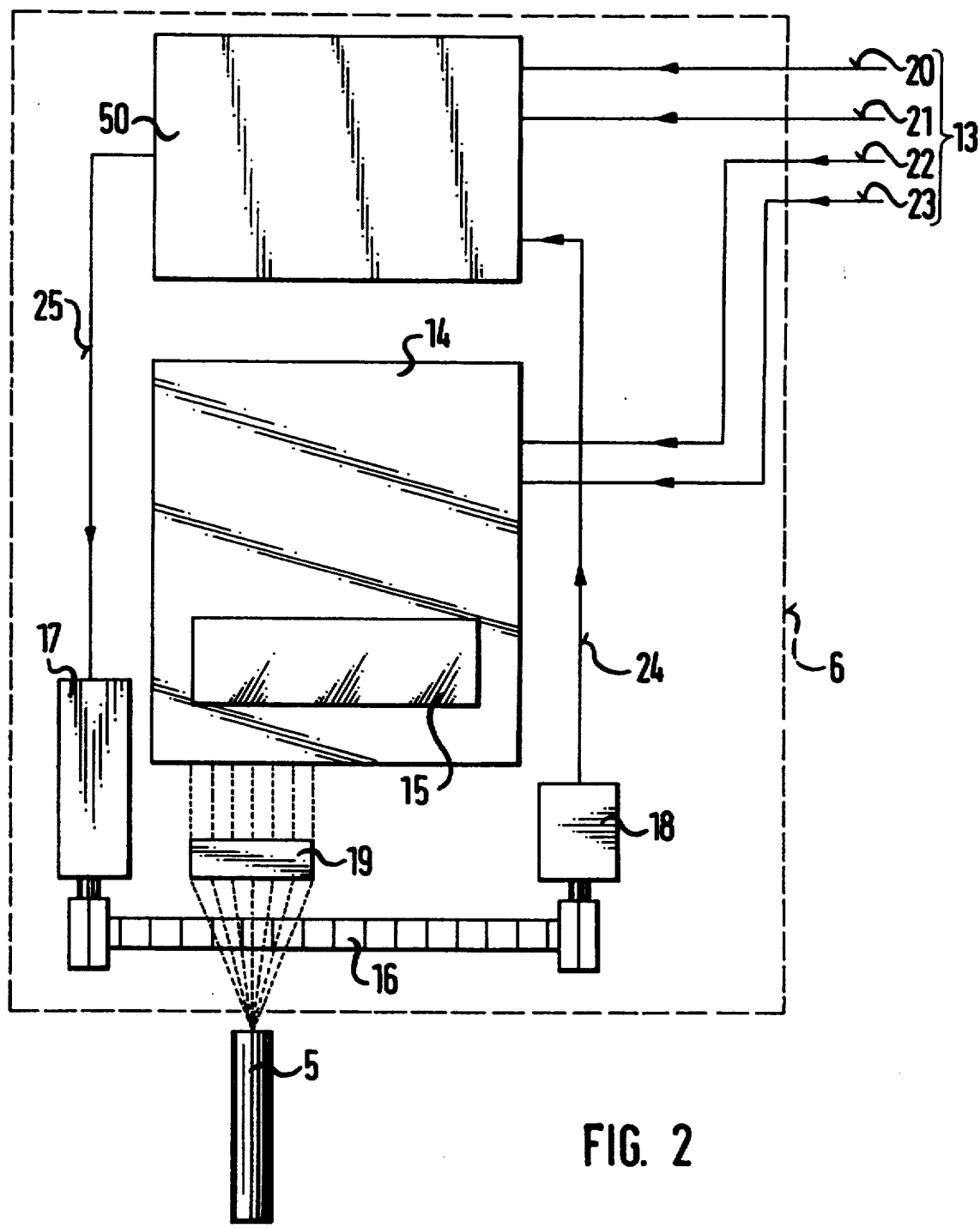
FIG. 2 shows the simplified, basic construction of the light source apparatus.

FIG. 2 shows schematically the basic construction and the control of the light source apparatus 6. This apparatus comprises a light-producing unit 14 with a filter device 15, a diaphragm 16, a motor 17 for driving the diaphragm 16, a potentiometer 18 coupled rigidly to the diaphragm 16, a focusing lens 19, which focuses the light from the unit 14 on the light conductor cable 5, and a control device 50 for adjusting the access opening of the diaphragm 16. The control lead device 13 connected to the apparatus 6 comprises the individual control leads 20, 21, 22 and 23, which are connected accordingly to the diaphragm control device 50 and to the light-producing unit 14. The potentiometer is connected via a lead 24 to the device 50, from which a lead 25 leads to the motor 17. The control device 50 obtains a voltage corresponding to the brightness of the relevant video image from the video signal from the lead 20. The control voltage for the diaphragm motor 17 is produced from this voltage. The diaphragm 16 is opened or closed depending on the value of the control voltage, until the optimum brightness of the light emerging from the unit 14 is achieved. The potentiometer 18 coupled rigidly to the wheel-shaped diaphragm determines the diaphragm position which is included to produce the control voltage for the diaphragm motor 17. The unit 14 is controlled via the lead 22 in the light mode of operation, in particular whether white continuous light or sequential coloured light is required. The filter device 15 is controlled via the synchronisation lead 23, in order to be able to feed, as authorised, sequential coloured light without errors into the light conductor cable 5, as also becomes clear.

Figure 3:
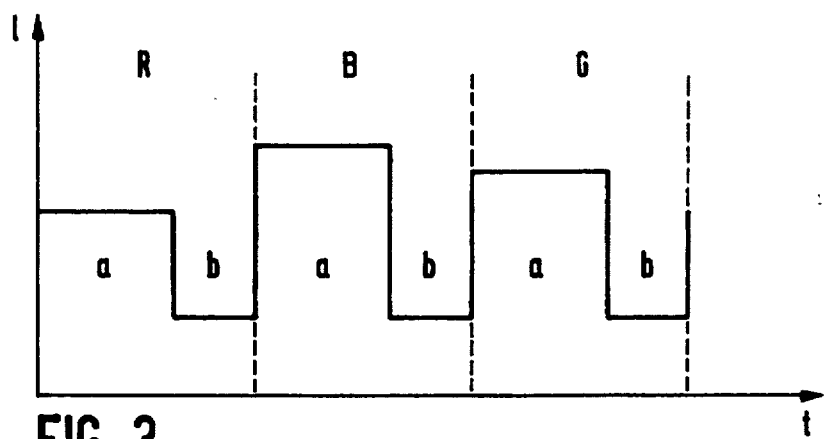
FIGS. 3 and 4 show the current curves for the current supply of the light source apparatus.
Figure 4:
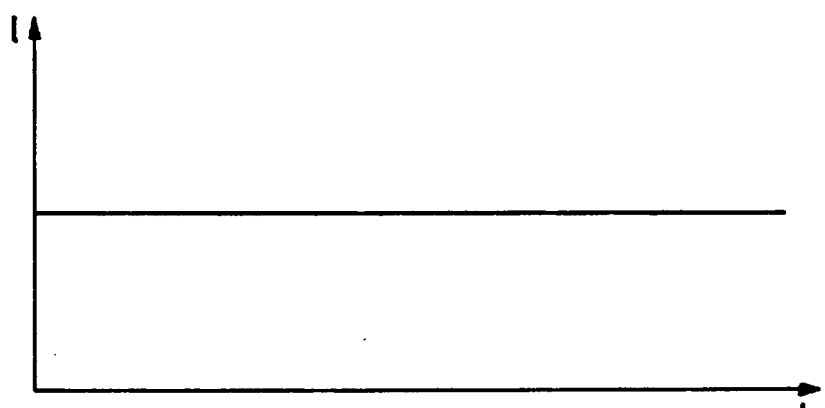

FIGS. 3 and 4 show the current curves for the lamp current of the light-producing unit 14. It can be seen that the lamp current has an essentially rectangular path according to FIG. 3 in the case of "sequential coloured light" mode of operation. The particular CCD element is illuminated during the times a, whereas this element is sorted during the times b. The lamp current is thus reduced to a minimum during the sorting phase, and this results in it being possible to operate the lamp of the unit 14 during the illumination phase at a greater current than the nominal current. This results in increased efficiency of the light-producing unit 14. According to FIG. 4, the lamp current is at a constant level for the "white continuous light" mode of operation.

Figure 5:
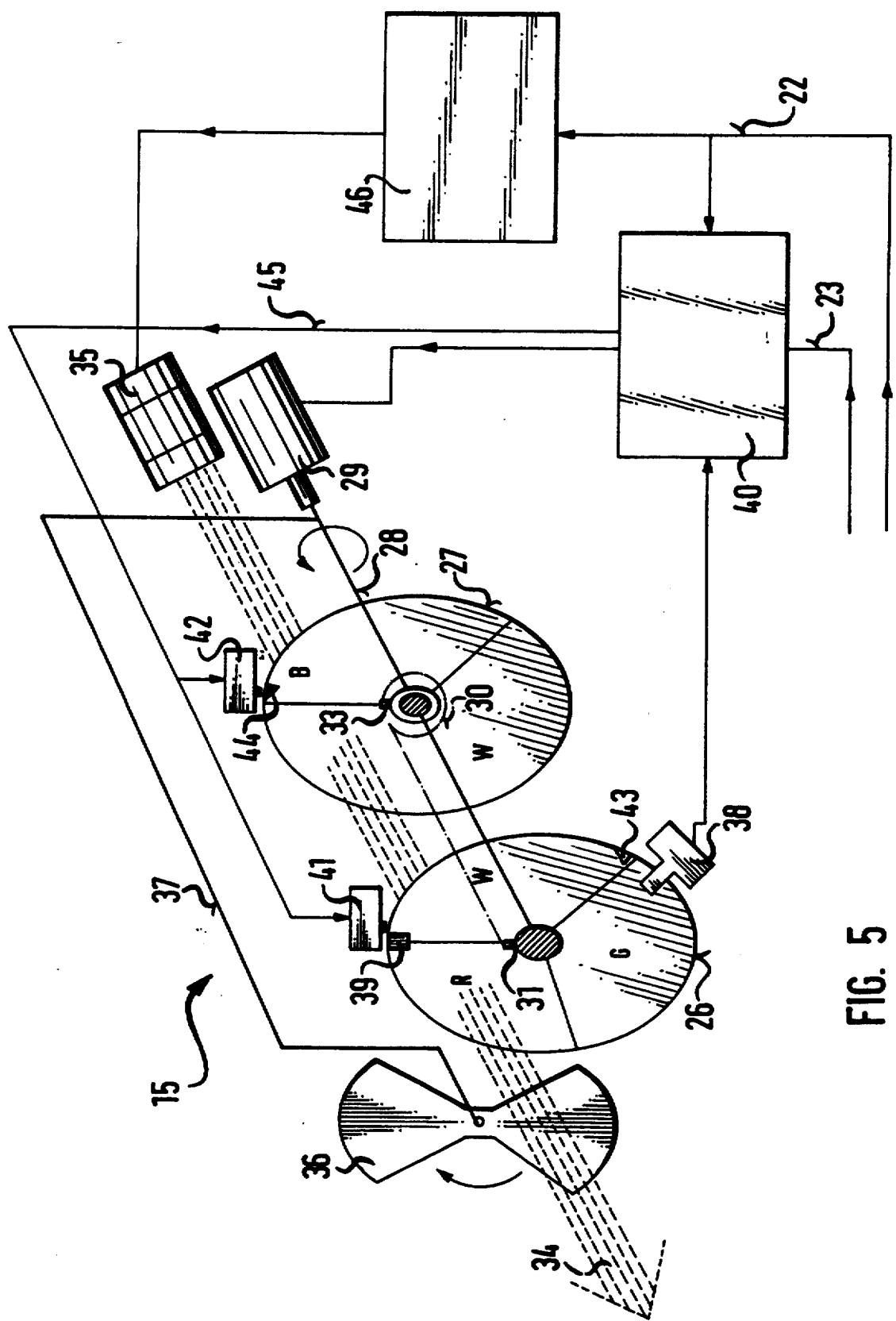
FIG. 5 shows a first embodiment of a filter device for the light source apparatus.

The first embodiment of a filter device 15 indicated schematically in FIG. 2 is shown in detail in FIG. 5. It shows a first wheel-shaped filter disc 26 and behind it a second wheel-shaped filter disc 27, both filter discs being arranged on a common drive shaft 28 which is driven by an electromotor 29. The first filter disc 26 is arranged on the shaft 28 to be resistant to rotation; the second filter disc 27 is arranged to be freely rotatable on the shaft 28. Both filter discs 26, 27 are coupled by means of a spring device 30, such that the two filter discs can be rotatably adjusted relative to one another. It is clear that both discs 26, 27 are rotated synchronously if the shaft 28 is driven. Whereas the first disc 26 is provided with a stop 31 in its central region, the second disc 27 likewise has a stop 33 in its central region. The stop 33 cooperates with the stop 31 in order to precisely set the first operating position of the two filter discs with respect to one another.

The first filter disc 26 is also equipped with three equal colour segments red R, green G and white W bordering on one another, these colour segments spanning an angular dimension of preferably 120°. The second filter disc 27 is equipped with a white colour segment W, which preferably spans 240°, and with a blue colour segment B, which preferably spans an angular dimension of 120°. The colour segments of the two filter discs oppose one another directly axially in the first operating position shown in FIG. 5, such that the white colour segment W of the first filter disc 26 covers the blue colour segment B of the second filter disc. Since the two filter discs conventionally lie in the ray path 34 of the lamp 35 of the light-producing unit 14 emitting white light, it is clear that sequential light is emitted in this case for common rotation of the two filter discs.

If it is required, a rotating impeller wheel 36 may be arranged in front of the first filter disc 26 in order to obtain an improved illuminating light curve in connection with the emission of sequential coloured light, as described in conjunction with German patent 3 908 366, to which reference is made herewith. The impeller wheel 36 is thus preferably likewise driven by the motor 29 via a drive lead 37.

Furthermore, a light barrier 38 is assigned to the edge region of the first filter disc 26, wherein the edge of the disc 26 is provided with a mark 39. The light barrier 38 is in turn connected to a control device 40 for the filter discs which also cooperates with the electromotor 29. If the filter disc 26 rotates, the mark 39 moves continuously past the light barrier 38, so that it relays a pulse train to the control device 40. The device 40 now compares the pulse train of the light barrier 38 to the pulse train of the videoscope processor 12 which enters via the synchronisation lead 23. The control device 40 then increases or lowers the control voltage for the motor 29 driving the filter discs 26, 27 for as long as the synchronisation pulse train agrees precisely with the pulse train of the light barrier. This produces as a result rotation of the filter discs 26, 27 synchronised with the videoscope processor 12.

The position of the filter discs 26, 27 shown in FIG. 5 represents their first operating position with respect to one another. This position is, as already indicated, determined by the spring device 30, by means of which both discs 26, 27 are coupled to one another, and by the stops 31 and 33 which rest against one another due to the force of the spring device 30. The two filter discs 26, 27 are shown at a greater distance from one another only for reasons of clarity, so that the stops are not shown to be resting against one another.

Furthermore, a fixing device is assigned to the filter discs 26, 27 for setting their second operating position. This fixing device comprises in each case one locking mechanism 41, 42 for each filter disc and one locking notch 43 and 44 in the filter discs 26 or 27 in the case shown here. The locking notch 43 is thus provided according to FIG. 5 in the lower end region of the white colour segment of the filter disc 26. The locking notch 44 of the other filter disc 27 is provided according to FIG. 5 in the upper region of the blue colour segment of the filter disc 27. Accordingly, the two locking notches are arranged to be offset to one another at an angular distance of 120°. The two locking mechanisms 41, 42 are actuated by the control device 40 via a lead 45.

The two locking mechanisms 41 and 42 are actuated to occupy their second operating position with respect to one another, that is during the "white continuous light" mode of operation. For this the "white continuous light" mode of operation is initially set at the device of the invention, and the constant lamp current according to FIG. 4 is then provided by a power supply 46 of the light-producing unit 14. The control device 40 then controls the motor 29 at a lower voltage, so that the two filter discs 26, 27 rotate more slowly or slow. The two locking mechanisms 41, 42 are then actuated, wherein the locking bodies of the locking mechanisms engage in the locking notches 43, 44. The second filter disc 27 is thus retained in the position according to FIG. 5, so that the white colour segment W of the second filter disc is situated in the ray path 34 of the lamp 35. The first filter disc 26 is rotated further out of the position shown in FIG. 5, so that the locking notch 43 passes upwards and the locking body of the locking mechanism 41 penetrates the locking notch 43 and thus fixes the first filter disc. In this position the white colour segment W of the filter disc 26 is then likewise situated in the ray path 34 of the lamp 35, because this filter disc is rotated by 120 angular degrees with respect to the second filter disc 27. The motor 29 experiences a higher load as a result of the thus effected stoppage of the drive shaft 28. This higher load is recognised by the control device 40, as a result of which the motor 29 is switched off. White continuous light is then emitted from the lamp 35 or from the light source apparatus 6. It is clear that the two filter discs are thus not covered by the impeller wheel 36.

Figure 6:
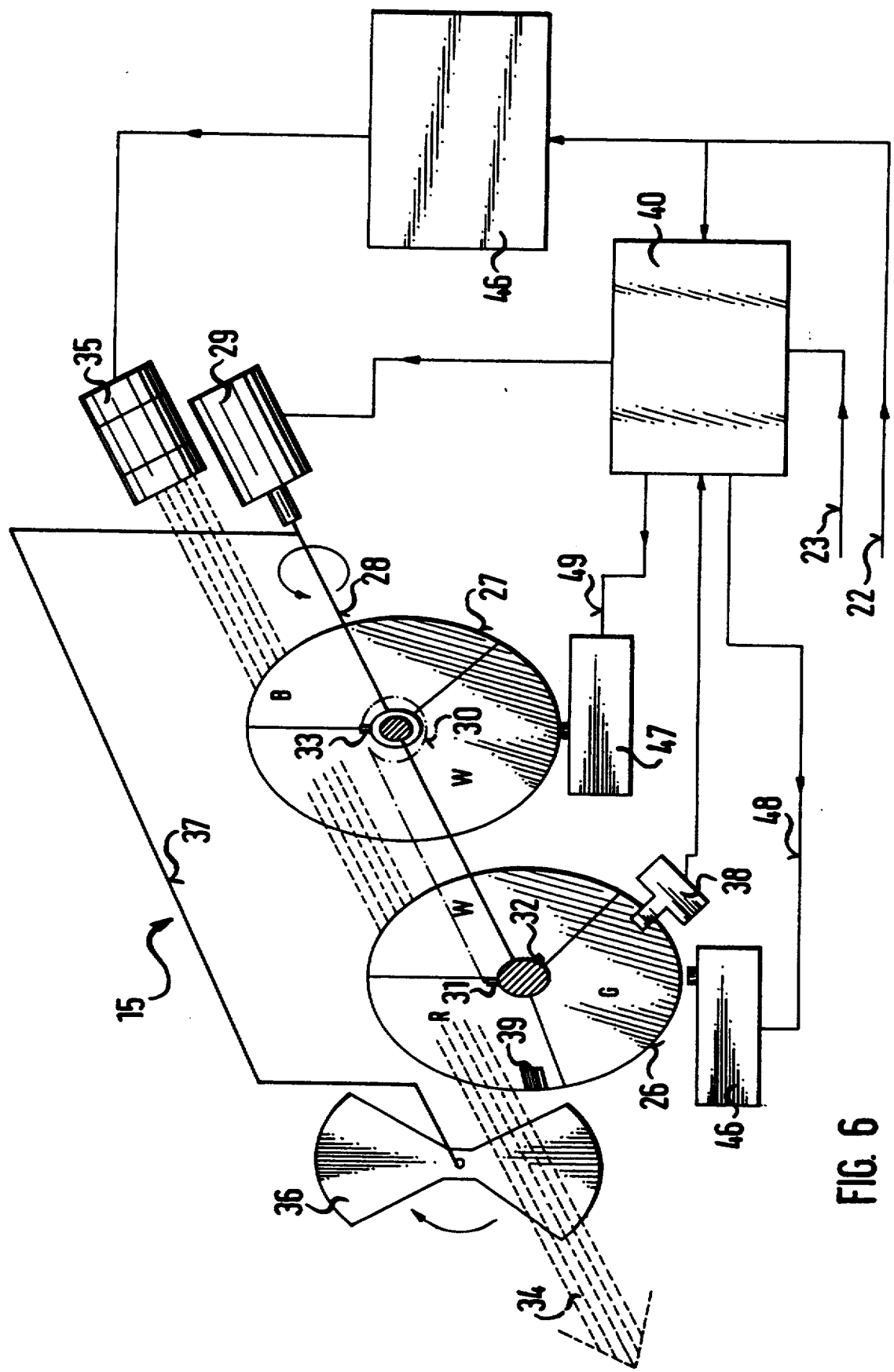
FIG. 6 shows a second embodiment of a filter device for the light source apparatus.

FIG. 6 shows an altered embodiment of the filter device 15 according to FIG. 5, wherein the same reference numbers are used for the same parts. The considerable changes consist in that friction brakes 46, 47 are provided as a fixing device for the filter discs 26 or 27 in this example instead of the aforementioned locking devices. These brakes are controlled by the control device 40 via leads 48, 49 and are preferably in operative connection with the peripheral edge of the filter discs. The use of brakes has the advantage that locking notches are omitted from the periphery of the filter discs, so that the filter discs have better synchronism properties.

In the case shown the "sequential coloured light" mode of operation is set, as can be seen from observing the position of the filter discs 26, 27, that is the colour segments red, green and blue follow one after another. For the "white continuous light" mode of operation, the appropriate switch of the light source apparatus 6 is switched over so that a corresponding signal is given to the control device 40 via the mode of operation lead 22. The control device 40 then supplies the motor 29 with a lower voltage potential, so that the drive shaft and hence also the filter discs 26, 27 rotate more slowly. If the mark 39 of the first filter disc 26 passes the light barrier 38, the control device 40 receives a corresponding pulse and the device 40 then activates the brake 47 for the second filter disc 27 via the lead 49, so that this filter disc is initially retained. Since the first filter disc 26, which has a second stop 32 in this example, is rotated further, the second stop 32 thereof moves against the stop 33 of the first filter disc while overcoming the force of the spring device 30. The first filter disc 26 has thus been rotated by an angular dimension of 120° corresponding to the angular dimension of the colour segment W of the first filter disc with respect to the second filter disc 27. The white colour segment W of the first filter disc 26 is thus again aligned to be axis-parallel to the white colour segment W of the second filter disc 27.

Both filter discs then rotate further synchronously, for which purpose the brake 47 is contacted so that it permits rotation of the second filter disc 27, but the position thereof does not change with respect to the first filter disc 26. Since the mark 39 of the first filter disc 26 is arranged at a predetermined peripheral distance in front of the white colour segment W of the first filter disc and hence is a measure of the axis-parallel alignment of the white colour segments of the two filter discs, the next time the mark 39 passes by the light barrier 38 the latter gives a further pulse to the control device 40, which then activates the brake 46 for the first filter disc 26 via the lead 48 and stops this filter disc and switches off the motor 29. The white colour segments of the two filter discs now lie in the ray path 34 of the lamp 35, so that white continuous light is available at the outlet of the light source apparatus 6.

If sequential coloured light is required again, the control device 40 receives an appropriate signal which ensures that the brakes 46 and 47 are rendered inactive and are therefore released from the filter discs, because of actuating the corresponding reversing switch on the light source apparatus 6 via the mode of operation lead 22. The spring device 30 will then set the second filter disc 27 again so that the blue colour segment B thereof again covers the white colour segment W of the first filter disc.

The present invention may be embodied in other specific forms without departing from the spirit or essential attributes thereof and, accordingly, reference should be made to the appended claims rather than to the foregoing specification as indicating the scope of the invention.

We claim:

1. A device for supplying light to endoscopes having a light source apparatus, said light source apparatus feeding into the endoscopes sequential colored light in a first operating position or white continuous light in a second operating position by means of a filter having several color surface regions and two filter discs which can be rotary driven, characterized in that:
- one of said two filter discs is provided with first and second segments, each of said first and second segments having a primary color, and a third segment having no color;
- the other of said two filter discs is provided with a fourth segment having a primary color and a fifth segment having no color; and
- both of said two filter discs are arranged to be rotatable on a common rotary axis and adjustable relative to one another and fixable such that said third segment covers said fourth segment in the first operating position of said two filter discs, and said third segment is aligned along the rotary axis with said fifth segment in the second operating position of said two filter discs.

2. The device according to claim 1, characterized in that one of said two filter discs is arranged to be rigid on a drive shaft and the other of said two filter discs is arranged to be freely rotatable on said drive shaft, and in that both of said two filter discs are coupled to one another by means of a spring.

3. The device according to claim 1, characterized in that one of said two filter discs has a first stop or second and third stops at a distance from one another, and the other of said two filter discs has a fourth stop cooperating with said first stop or said second and third stops for setting the first and second operating positions of the filter discs.

4. The device according to claim 1, characterized in that fixing means is provided for said two filter discs for setting said second operating position.

5. The device according to claim 4, characterized in that said fixing means comprises a locking mechanism for each of said two filter discs provided with a locking notch.

6. The device according to claim 4, characterized in that said fixing means comprises one brake for each of said two filter discs.

7. The device according to claim 1, characterized in that said third segment spans an angular dimension of 120 degrees, whereas said fifth segment spans an angular dimension of 240 degrees.

8. The device according to claim 1, characterized that said fourth segment spans an angular dimension of 120 degrees.

9. The device according to claim 1, characterized in that a control device is provided for adjusting and operating said two filter discs.

* * * * *